United States Patent [19]

VandenBerg

[11] Patent Number: Plant 7,585

[45] Date of Patent: Jul. 9, 1991

[54] CHRYSANTHEMUM PLANT NAMED DARK CHARM

[75] Inventor: Cornelis P. VandenBerg, Salinas, Calif.

[73] Assignee: Yoder Brothers, Inc., Barberton, Ohio

[21] Appl. No.: 409,454

[22] Filed: Sep. 18, 1989

[51] Int. Cl.[5] ..... A01H 5/00

[52] U.S. Cl. ..... Plt./76

[58] Field of Search ..... Plt./76, 80, 81

[56] References Cited

U.S. PATENT DOCUMENTS

| | | | |
|---|---|---|---|
| P.P. 4,960 | 11/1982 | Meek et al. | Plt. 76 |
| P.P. 5,350 | 11/1984 | Duffett | Plt. 76 |
| P.P. 5,502 | 6/1985 | Duffett | Plt. 76 |
| P.P. 5,777 | 8/1986 | Duffett | Plt. 76 |
| 4,616,099 | 10/1986 | Sparkes | 47/58 |

OTHER PUBLICATIONS

Broertjes et al., 1980, "A Mutant of a Mutant of a Mutant of a . . . Irradiation of Progressive Radiation-Induced Mutants in a Mutation Breeding Programme with *Chrysanthemum morifolium*", Euphytica, 29 (1980):525-530.

Gosling, ed., 1979, "The Chrysanthemum Manual", The National Chrysanthemum Society, Essex Telegraph Press Ltd., London, pp. 329-336.

Broertjes et al., 1978, "Application of Mutation Breeding Methods in the Improvement of Vegetatively Propagated Crops", Elsevin Sci. Pub. Co., New York, pp. 162-175.

Searle et al., 1968, "Chrysanthemums the Year Round", Blandford Press Ltd., London, pp. 26-29, 320-327.

Broertjes, 1966, "Mutation Breeding of Chrysanthemums", Euphytica, 15 (1966):156-162.

Chan, 1966, "Chrysanthemums and Rose Mutations Induced by Xrays", Am. Soc. Hort. Sci., vol. 88 (1966):613-620.

*Primary Examiner*—Howard J. Locker

*Attorney, Agent, or Firm*—Foley & Lardner, Schwartz, Jeffery, Schwaab, Mack, Blumenthal & Evans

[57] ABSTRACT

A Chrysanthemum plant named Dark Charm particularly characterized by its flat capitulum form; decorative capitulum type; purple-violet ray floret color; diameter across face of capitulum of up to 11 cm at maturity when grown as a pinched disbudded pot mum; uniform eight week photoperiodic flowering response to short days; medium plant height when grown as a pinched pot mum; and spreading branching pattern.

3 Drawing Sheets

The present invention comprises a new and distinct cultivar of Chrysanthemum, botanically known as *Dendranthema grandiflora,* and referred to by the cultivar name Dark Charm.

Dark Charm, identified as 79-I34P04, is a product of a mutation induction program which had the objective of creating new Chrysanthemum cultivars that would expand the color range of an existing cultivar while retaining all other traits.

Dark Charm was discovered and selected by Cornelis P. VandenBerg in December, 1986 in a controlled environment in Salinas, Calif. as one flowering plant within a flowering block established as rooted cuttings from stock plants which had been exposed as unrooted cuttings to an x-ray source of 2000 rads. The irradiated parent was an unnamed mutation, which was derived from an earlier irradiation of the cultivar identified as Charm, disclosed in U.S. Plant Pat. No. 5,502.

The first act of asexual reproduction of Dark Charm was accomplished when vegetative cuttings were taken from the initial selection in March, 1987 in a controlled environment in Salinas, Calif., by technicians working under formulations established and supervised by Cornelis P. VandenBerg.

Horticultural examination of controlled flowerings of successive plantings has shown that the unique combination of characteristics as herein disclosed for Dark Charm are firmly fixed and are retained through successive generations of asexual reproduction.

Dark Charm has not been observed under all possible environmental conditions. The phenotype may vary significantly with variations in environment such as temperature, light intensity and daylength.

The following observations, measurements and comparisons describe plants grown in Salinas, Calif. and Leamington, Canada, under greenhouse conditions which approximate those generally used in commercial greenhouse practice.

The following traits have been repeatedly observed and are determined to be basic characteristics of Dark Charm, which, in combination, distinguish this Chrysanthemum as a new and distinct cultivar:

1. Flat capitulum form.
2. Decorative capitulum type.
3. Purple-violet ray floret color.
4. Diameter across face of capitulum up to 11 cm at maturity, when grown as a pinched disbudded pot mum.
5. Uniform eight week photoperiodic flowering response to short days.
6. Medium plant height, requiring 0 to 7 long days after pinch prior to short days and 1 application of 2500 ppm B-9 SP to attain a flowered plant height of 25 to 35 cm for year-round flowerings when grown as a pinched pot mum.
7. Spreading branching pattern.

The accompanying photographic drawings show typical inflorescence and leaf characteristics of Dark Charm, with the colors being as nearly true as possible with illustrations of this type.

Sheet 1 is a color photograph of Dark Charm grown as a pinched disbudded pot mum grown in a 15 cm pot.

Sheet 2 is a black and white photograph of three views of the inflorescence of Dark Charm.

Sheet 3 is a black and white photograph showing the upper and under sides of the leaves of Dark Charm at three stages of development (mature, intermediate and immature).

Of the commercial cultivars known to the inventor, the most similar in comparison to Dark Charm is the cultivar Charm. All traits of Dark Charm are similar to those of Charm, except the color of ray florets. The color of the ray florets of Dark Charm is significantly darker than the color of Charm.

In the following description, color references are made to The Royal Horticultural Society Colour Chart. The color values were determined on plant material grown as a pinched disbudded pot mum in Salinas, Calif. on June 7, 1989.

Classification:

*Botanical.*—*Dendranthema grandiflora* cv Dark Charm.

*Commercial.*—Decorative disbudded pot mum.

INFLORESCENCE

A. Capitulum:

*Form.*—Flat.

*Type.*—Decorative.

*Diameter across face.*—Up to 11 cm at maturity.

B. Corolla of ray florets:

*Color (general tonality from a distance of three meters).*—Purple-violet.

*Color (upper surface).*—80B to 80C, slightly overlaid with 74B. Outer petals fade to 80D.

*Color (under surface).*—80D.

*Shape.*—Flat, oblong.

C. Corolla of disc florets:

*Color (mature).*—Closest to 1A.

*Color (immature).*—Closest to 151D.

D. Reproductive organs:

*Androecium.*—Present on disc florets only, very few; scant pollen.

*Gynoecium.*—Present on both ray and disc florets.

PLANT

A. General appearance:

*Height.*—Medium; 25 to 35 cm as a pinched disbudded pot mum with 0 to 7 long days after pinch prior to short days and 1 application of 2500 ppm B-9 SP when grown in a 15 cm pot.

*Branching pattern.*—Spreading.

B. Foliage:

*Color (upper surface).*—147A.

*Color (under surface).*—147B.

*Shape.*—Moderately lobed and deeply serrated.

I claim:

1. A new and distinct Chrysanthemum plant named Dark Charm, as described and illustrated.

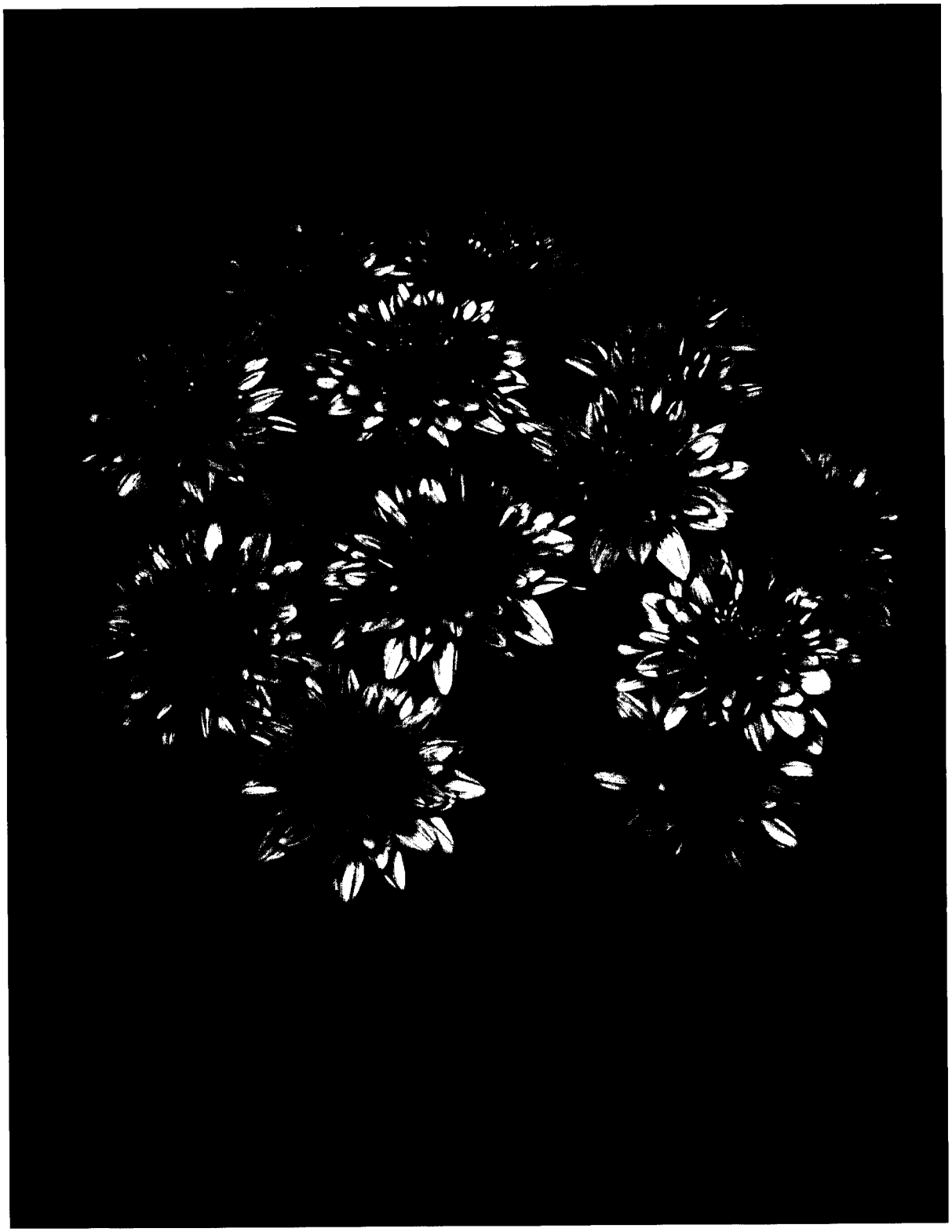

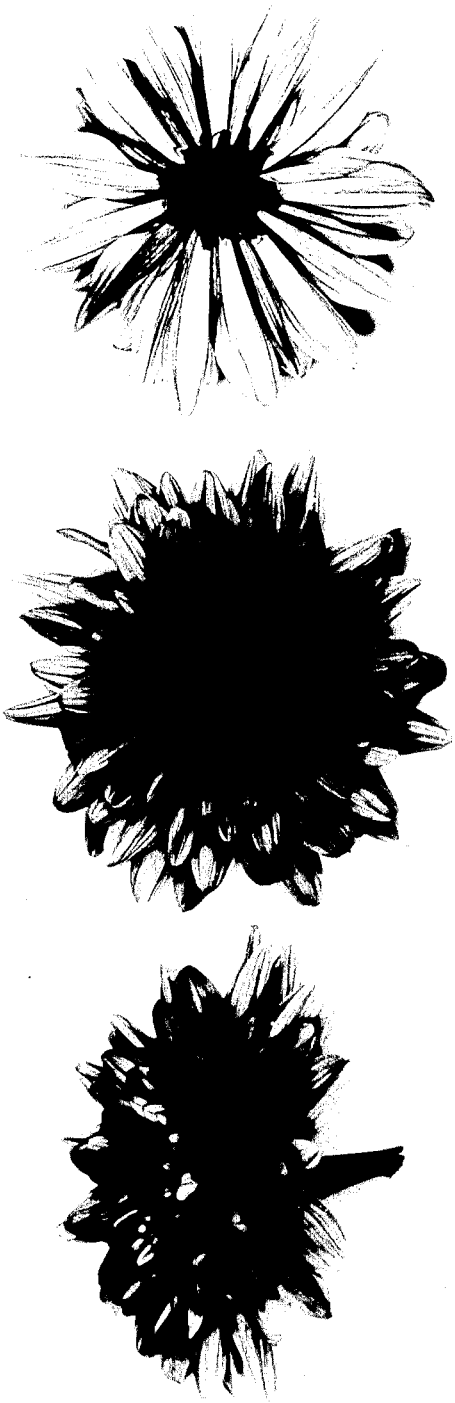

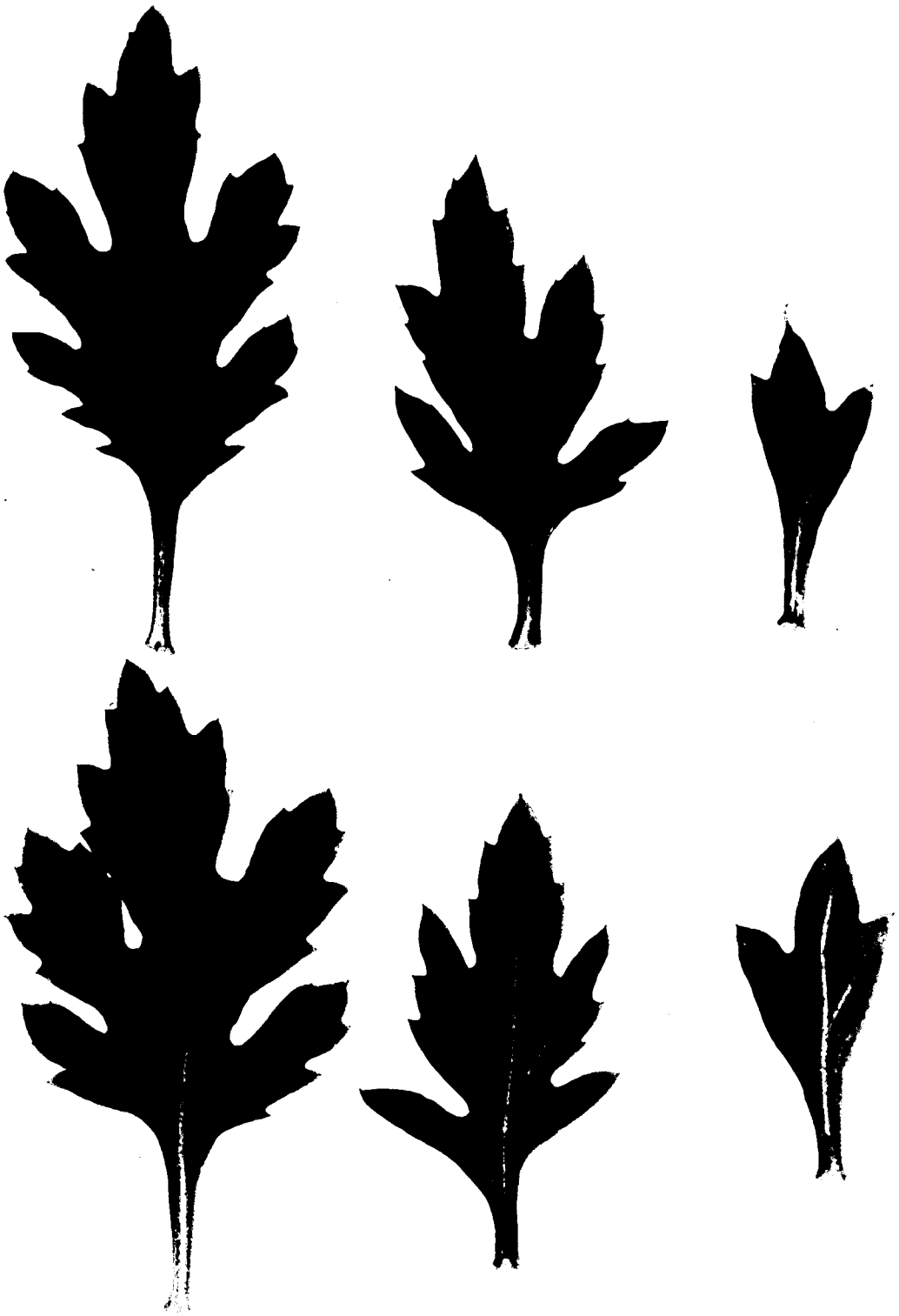

* * * * *